(12) United States Patent
Yu

(10) Patent No.: US 7,133,723 B2
(45) Date of Patent: Nov. 7, 2006

(54) DEVICE FOR ENHANCING CELL METABOLISM

(75) Inventor: Eukki Qi Yu, City of Industry, CA (US)

(73) Assignee: Misty Li-Ming Chang, City of Industry, CA (US)

( * ) Notice: Subject to any disclaimer, the term of this patent is extended or adjusted under 35 U.S.C. 154(b) by 1 day.

(21) Appl. No.: 10/856,524

(22) Filed: May 28, 2004

(65) Prior Publication Data

US 2005/0267548 A1    Dec. 1, 2005

(51) Int. Cl.
*A61N 1/18* (2006.01)
(52) U.S. Cl. ............................. 607/50; 607/67; 607/72
(58) Field of Classification Search ................ 607/2, 607/50, 68–73, 145, 66; 606/9
See application file for complete search history.

(56) References Cited

U.S. PATENT DOCUMENTS

| 3,958,577 | A | * | 5/1976 | Rodler ........................ 607/67 |
| 5,512,057 | A | * | 4/1996 | Reiss et al. ................... 607/67 |
| 6,275,735 | B1 | * | 8/2001 | Jarding et al. ................ 607/53 |
| 6,584,358 | B1 | * | 6/2003 | Carter et al. ................. 607/69 |
| 6,675,048 | B1 | * | 1/2004 | McGraw et al. .............. 607/51 |
| 6,826,429 | B1 | * | 11/2004 | Johnson et al. .............. 607/67 |

OTHER PUBLICATIONS

APS Therapy, Direct Current operated Micro Current Device. ☐☐Nov. 22, 2001☐☐Http://www.apstherapy.com/apsmain.htm.*
The Buzz Over Electric Wrinkle Remover Los Angeles Times, Feb. 2, 1998.*
WO 99/06106, Swanepoel, Christoffel, Apparatus For Electrical Stimulation Of A Body, Feb. 11, 1999.*

* cited by examiner

Primary Examiner—Robert E. Pezzuto
Assistant Examiner—Tammie K. Heller
(74) Attorney, Agent, or Firm—Raymond Y. Chan; David and Raymond Patent Firm

(57) ABSTRACT

The cell enhancing device for an electrical pulse cosmetic meter, wherein the composite pulse generating device comprising an electrical pulse generating device, generating an electrical pulse sequence of a predetermined electrical pulse amplitude, wherein a frequency of said electrical pulse sequence is adjustable, a waveform adjuster, converting said electrical pulse sequence to a composite pulse sequence, and outputting said composite pulse sequence to a cosmetic head of said electrical pulse cosmetic meter. The present invention has the advantages of being small in size and light in weight. Furthermore, it greatly enhances circulation in skin structure of body, so as to achieve effective cosmetic results.

3 Claims, 7 Drawing Sheets

DEVICE FOR ENHANCING CELL METABOLISM

BACKGROUND OF THE PRESENT INVENTION

1. Field of Invention

The present invention relates to a device for enhancing cell metabolism, and more particularly to a composite pulse generating device for an electrical pulse cosmetic meter, wherein the composite pulse generating device comprising an electrical pulse generating unit, a waveform adjuster and a treatment body. The waveform adjuster converts an electrical pulse sequence produced by the electrical pulse generating device to a composite pulse sequence, and outputs the composite pulse sequence to the cosmetic head. The frequency of the composite pulse sequence matches with the natural frequency of a cardiovascular cycle. As a result the vibration frequencies of cells are tuned to that of the cardiovascular cycle, such that blood flow is enhanced.

2. Description of Related Arts

Body metabolism rate slows down with age. This slowing down of metabolism will show in all aspects of the body, including deterioration in health, energy level, gaining in weight and so on. It is, however, most noticeable on the skin.

Water and impulses from nerves are essential for skin cells to stay alive. Water is the main constituent of blood, which bring nutrients to all living cells. Impulses are produced by nerves connecting to the brain, which provides instructions and controls activities in cells. When in lack of either one of them, skin cells die off.

Many research shows that aging is related to an increasing production of oxidative free radicals. Such oxidative free radicals are, in turn, related to many health problems associated with aging, such as higher chances of getting Caners, atherosclerosis, heart disease and many other chronic diseases. They are substances produced by the mitochondria respiration in a cell. The older an individual, the more oxidative free radicals are produced.

The slowing down of metabolism is controlled by three factors, the first being the body genes, which acts as a program to the body's biological clock. The second is the person's subconscious, which is affect by the surrounding environment. The third is damaged cells or organs, which ability of renewing dead cells deteriorates.

When metabolism rate slows down, it means that body cells die off at a higher rate than they can be regenerated. In the case of skin cells, the rate of new skin cells being created are not as high as that of cells dying off. As a result, wrinkles appear on the skin.

Wrinkles is the most obvious indication of aging, which is the reason why people are very willing to pay hundreds and thousands of dollars on facial treatments to prevent getting or in the hope of getting rid of wrinkles. All sorts of creams and treatment lotions are produced claiming their miraculous effects on wrinkles and skin conditions. However, their results are questionable.

Others would even go as far as having cosmetic surgeries, such as having a face lift, to smoothen their wrinkles. Despite how safe cosmetic surgeons claim, all surgeries have risks. And, in general, they are all very costly. Furthermore, such wrinkle removing treatments and surgeries can only remove wrinkles and cannot prevent the reoccurrence of wrinkles or improve on the skin conditions after removing the wrinkles. As a result, such treatments and surgeries are only temporary. The fundamentals of the occurrence of wrinkles are not being dealt with.

As a result, in order to prevent or remove wrinkles in a safer, more effective, more cost effective and convenient manner, better treatments that can deal with the causes of wrinkles has to be provided.

SUMMARY OF THE PRESENT INVENTION

A main object of the present invention is to provide a device for enhancing cell metabolism, comprising a composite pulse generating device, which provides a composite pulse sequence to communicate with the body cells, so as to target at the fundamental cause of the slowing of metabolism, relieving the symptoms of aging and suppressing the production of oxidative free radicals.

Another object of the present invention is to provide a device for enhancing cell metabolism, wherein the frequency of the composite pulse produced is adjustable according to the different natural frequency of the cardiovascular cycles of different users.

Another object of the present invention is to provide a device for enhancing cell metabolism, wherein the composite generating device is controlled by integrated circuit, minimizing the size of the device so as to provide users with greater convenience.

Another object of the present invention is to provide a device for enhancing cell metabolism which uses batteries as a power source, allowing users to conveniently make use of anywhere.

Accordingly, in order to accomplish the above objects, the present invention provides a cell enhancing device for enhancing human cell metabolism, comprising:

a treatment body having a treating head for contacting a skin of a user;

a pulse generating unit electrically connected to a power source for generating an electric pulse; and a waveform adjuster electrically connected to the pulse generating unit for selectively tuning the electric pulse to form a composite pulse having an amplitude matching with a user's pulse, wherein the composite pulse is output at the treating head of the treatment body for communicating with a cell under the skin of the user so as to enhance a metabolism of said cell of the user.

The present invention has an alternative embodiment, wherein the present invention provides a method of enhancing human cell metabolism, comprising the steps of:

(a) generating an electric pulse;

(b) converting the electric pulse to form a composite pulse, wherein the composite pulse is selectively tuned to have an amplitude matching with a user pulse; and (c) applying the composite pulse on a skin of the user in such a manner that the composite pulse is adapted to communicating with a cell under the skin of the user so as to enhance a metabolism of the cell of the user.

These and other objectives, features, and advantages of the present invention will become apparent from the following detailed description, the accompanying drawings, and the appended claims.

DETAILED DESCRIPTION OF THE PREFERRED EMBODIMENT

The formation of wrinkles, marking the slowing of metabolism, is controlled by a number of factors: genes, the subconscious mind and the surrounding environment. Genes act a program providing metabolism information to all cells. The subconscious mind provides an additional signal to body cells, affecting the metabolism rate. Examples of surrounding environment are damaged blood vessels or toxic substances accumulated in the body, altering information provided by the genes.

As a result, applying cream and lotion to the skin or receiving cosmetic surgeries are not enough to remove wrinkles in a long run. They might be able to reduce the appearance of wrinkles for a short period of time because the real course of wrinkles had not been dealt with. To effectively get rid of wrinkles and staying young, the information provided by the genes to the cells must be altered, so as to enhance metabolism rate.

The composite pulse provided by the present invention is information transmitted to communicate with cells, overriding information provided by the genes, such that metabolism rate is enhanced. It also tunes the vibration frequency of the cells to the natural frequency of a user's cardiovascular cycle, such that blood can flow more smoothly into the cells, such that the cells remain well nourished.

Figure 1:
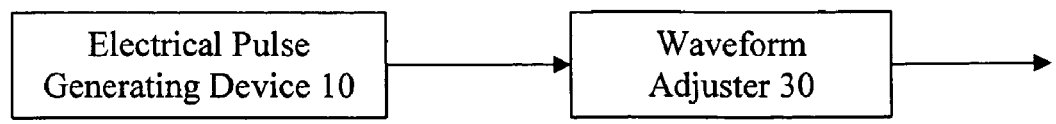
FIG. 1 is a flow chart illustrating the basic principle of the device for enhancing cell metabolism according to the preferred embodiment of the present invention.
Figure 2:
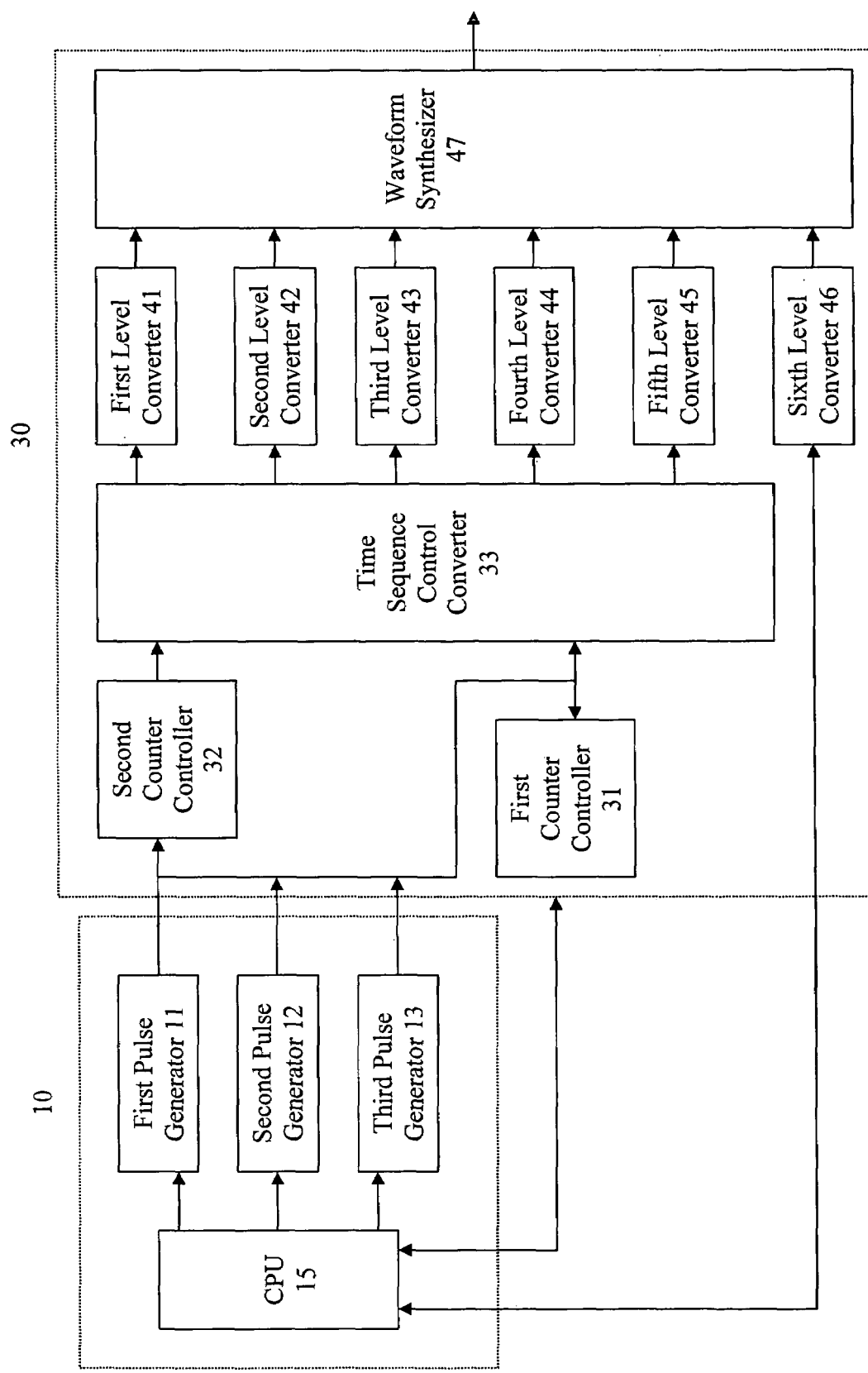
FIG. 2 is a circuit diagram of the device for enhancing cell metabolism according to the above preferred embodiment of the present invention.

Referring to FIG. 1 and FIG. 2 of the drawings, a device for enhancing cell metabolism according to a preferred embodiment of the present invention is illustrated, wherein the device comprises an electrical pulse generating device 10, a waveform adjuster 30 and a cosmetic functional head 40.

The electrical pulse generating device 10 produces an electrical pulse sequence with a predetermined amplitude. A frequency of the electrical pulse sequence can be altered as desired.

The waveform adjuster 30 converts the electrical composite pulse sequence produced by the electrical pulse generating device 10 into a composite pulse sequence. In general, a composite pulse is a series of overlapping pulses received from the same source over several paths in a pulse navigation system. The composite pulse sequence is then transferred to the cosmetic functional head 40 of the device for enhancing cell metabolism.

According to the circuit diagram as shown in FIG. 2, the electrical pulse generating device 10 comprises a power source 14, an integrated circuit 15, a first pulse generator 11 having a first frequency F1, a second pulse generator 12 having a second frequency F2, and a third pulse generator 13 having a third frequency F3, wherein the integrated circuit 15 controls the operations of the pulse generators 11, 12 and 13.

Each of the frequencies is a multiple of the other frequencies respectively. According to the preferred embodiment, the first frequency F1=666 KHz, the second frequency F2=1 MHz and the third frequency F3=2 MHz.

According to a preferred embodiment of the present invention, the power source 14 is a battery compartment connected to the electrical pulse generating device 10, such that batteries can be inserted to provide power to the electrical pulse generating device 10.

The waveform adjuster 30 comprises a first counter-controller 31, a second counter-controller 32, a time sequence control converter 33, a first level converter 41 having a first electrical level L1, a second level converter 42 having a second electrical level L2, a third level converter 43 having a third electrical level L3, a fourth level converter 44 having a fourth electrical level L4, a fifth level converter 45 having a fifth electrical level L5, a sixth level converter 46 having a sixth electrical level of 0V and a waveform synthesizer 47. The time sequence control converter 33 controls the first, second, third, fourth and fifth level converter 41–45. A level converter converts nonstandard logic input voltages to standard diode transistor logic or other logic levels.

Through the integrated circuit 15 and the waveform adjuster 30, a composite pulse of a desired magnitude is produced, such that the composite pulse matches with the natural frequency of a user's cardiovascular cycle.

The first counter-controller 31 is an m frequency dividing counter-controller, the second counter-controller 32 is an n frequency dividing counter-controller, while n/m=k, where n and m are positive integrals and k is a positive odd number.

The number of level converters (p) of the waveform adjuster 30 may vary according to p=k+1. According to this preferred embodiment, m=15, n=75, therefore k=5 and p=6. Also, electrical level L1 is 2V, electrical level L2 is 3V, electrical level L3 is 4V, electrical level L4 is 3V and electrical level L5 is 2V. The outputs from the first, second, third, fourth, fifth and sixth level converters are inputted into the waveform synthesizer 47. A composite pulse is synthesized by the waveform synthesizer 47 and is then outputted to the cosmetic functional head 40 of the device for enhancing cell metabolism.

According to FIG. 2 of the drawings, when the device is connected to a power source, the integrated circuit begin to function after initializing, controlling the first pulse generator 11 to produce a first square wave sequence having the frequency of F1. The first square wave sequence goes through the second counter-controller 32 and the time sequence control converter 33 and reaches the first level converter 41.

The time sequence control converter 33 controls the first level converter 41 to have conduction, while controlling the second, third, fourth, fifth and sixth level converter 42–46 to be shut off. As a result, the first square wave sequence produced by the first level converter 41 goes through the conducting first level converter 41 and transmitted to the waveform synthesizer 47. At the same time, the integrated circuit 15 controls the first counter-controller 31 and the second counter-controller 32 to carry out counting.

The second counter-controller 32 is an m frequency dividing counter-controller. According to the preferred embodiment, m=15. The second counter-controller 32 produces an instruction signal to the time sequence control converter 33 every m number of pulse. When the time sequence control converter 33 receives the instruction signal from the second counter-controller 32, the time sequence control converter 33 switches to the second level converter 42, hence shutting down the first level converter 41 and conducting the second level converter 42.

As a result, the first square wave sequence produced by the first pulse generator 11 goes through the conducting second level converter 42 and transmitted to the waveform synthesizer 47.

Under such operation, a pulse sequence formed by m pulse sequentially conducts through the first level converter 41, the second level converter 42, the third level converter 43, the fourth level converter 44 and the fifth level converter 45 respectively, to the waveform synthesizer 47. Each of the first, second, third, fourth and fifth level converters 41–45 also will output a pulse respectively. The frequency of the pulse is the same as the frequency of the output signal of the first pulse generator 11; the amplitude is limited by the first, second, third, fourth and fifth level converter 41–45 to have electrical levels L1–L5 respectively.

At this moment, the first pulse generator 11 continued to output n=k×m number of pulse. As the first counter-controller 31 is an n frequency dividing counter-controller, when the first pulse generator 11 has outputted n number of pulse, the first counter-controller 31 will produce an overflow signal, output a low electrical level signal to integrated circuit 15. After receiving the low electrical level signal from the first counter-controller 31, the integrated circuit 15 stops the first pulse generator 11 from operation, thereby reinstating the first counter-controller 31.

At the same time, the integrated circuit 15 outputs to the sixth level converter 46 a high level electrical signal for a length of time of t0, causing the sixth level converter 46 to output to the waveform synthesizer 47 a signal of converting electrical level L6=0V. According to the preferred embodiment, t0=20 ms.

After this first cycle, the waveform synthesizer 47 synthesized a first composite pulse sequence of frequency F1, where F1=666 KHz, wherein the composite pulse sequence has a shape of 3 steps, which has a symmetrical envelop line.

Then, the integrated circuit 15 controls the second pulse generator 12 to produce a pulse sequence with a frequency of F2. The waveform adjuster 30 operates in the same manner as it was when the first pulse generator 11 was in operation. After a second cycle which is the same as the first cycle, the waveform synthesizer 47 synthesized a second composite pulse sequence of frequency F2, where F2=1 MHz, wherein the composite pulse sequence has a shape of 3 steps, which has a symmetrical envelop line.

Then, the integrated circuit 15 controls the third pulse generator 13 to produce a pulse sequence with a frequency of F3. The waveform adjuster 30 operates in the same manner as it was when the first pulse generator 11 was in operation. After a third cycle which is the same as the first cycle, the waveform synthesizer 47 synthesized a third composite pulse sequence of frequency F3, where F3=2 MHz, wherein the composite pulse sequence has a shape of 3 steps, which has a symmetrical envelop line.

Under the control of integrated circuit 15, after the first, second and third cycle, the waveform synthesizer 47 outputs three composite pulse sequences of frequencies F1, F2 and F3 respectively, the time lag between each sequence is t0 respectively, wherein each of the sequences has a shape of 3 steps, having a symmetrical envelop line.

Figure 3:
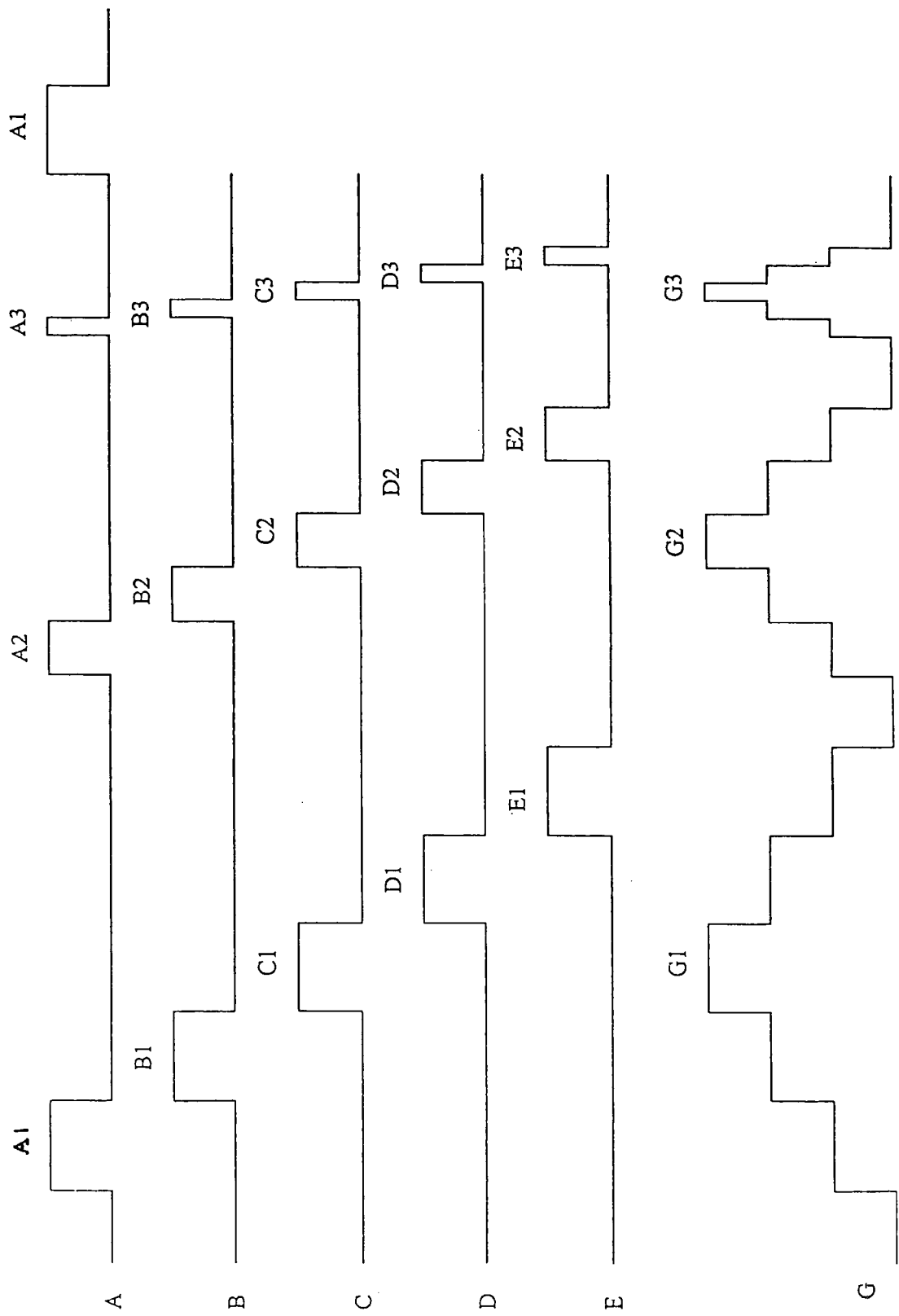
FIG. 3 illustrates the formation of composite pulse with the use of the device for enhancing cell metabolism according to the above preferred embodiment of the present invention.

FIG. 3 illustrates the process of formation of a composite pulse according to the preferred embodiment of the present invention. A first pulse sequence A1 of the line A illustrates the first pulse generator 11 produces a first pulse sequence having a frequency of F1 formed by m number of pulse, which, according to the preferred embodiment, is the first to fifteen pulse. The first pulse sequence is converted by the first level converter 41. The waveform synthesizer 47 outputs, as shown in Line G, the first step of the first composite pulse G1.

Similarly, a first pulse sequence B1 of the line B illustrates the first pulse generator 11 produces a second pulse sequence having a frequency of F1 formed by m number of pulse, which, according to the preferred embodiment, is the sixteenth to thirtieth pulse. The first pulse sequence is converted by the second level converter 42. The waveform synthesizer 47 outputs, as shown in Line G, the second step of the first composite pulse G1.

Similarly, a first pulse sequences C1, D1 and E1 of the line C, D and E respectively illustrates the first pulse generator 11 produces a third, fourth and fifth pulse sequence having a frequency of F1 formed by m number of pulse, which, according to the preferred embodiment, is the sixteenth to thirtieth pulse. The first pulse sequences are converted by the third level converter 43, the fourth level converter 44 and the fifth level converter 45 respectively. The waveform synthesizer 47 outputs, as shown in Line G, the third, fourth and fifth step of the first composite pulse G1.

As a result, the waveform synthesizer 47 outputs a first composite pulse sequence G1, as shown in Line G of FIG. 3, wherein the composite pulse sequence G1 has a frequency of F1, amplitude of L1–L5 respectively and has a shape of 3 steps, which has a symmetrical envelop line.

Similarly, the waveform synthesizer 47 outputs a second composite pulse sequence G2 and a third composite pulse sequence G3. The second composite pulse sequence G2 has a frequency of F2 and the third composite pulse sequence G3 has a frequency of F3. The time lag between the each of the first, second and third composite pulse sequence G1–G3 is t0 respectively.

Figure 4:
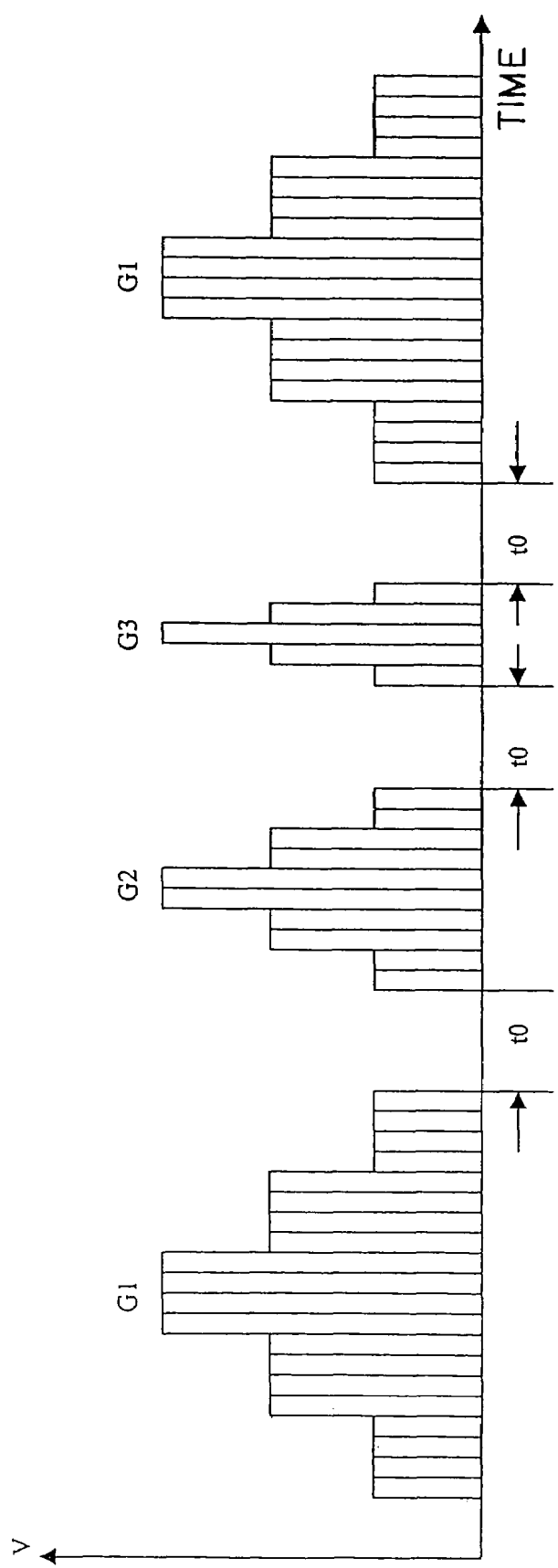
FIG. 4 illustrates a composite pulse formed by using the device for enhancing cell metabolism according to the above preferred embodiment of the present invention.

When the operation procedure as illustrated above is repeated continuously, the waveform synthesizer 47 will therefore produce an electrical pulse for the device according to the preferred embodiment of the present invention by the above composite pulse sequence G1–G3, as shown in FIG. 4.

Figure 5:
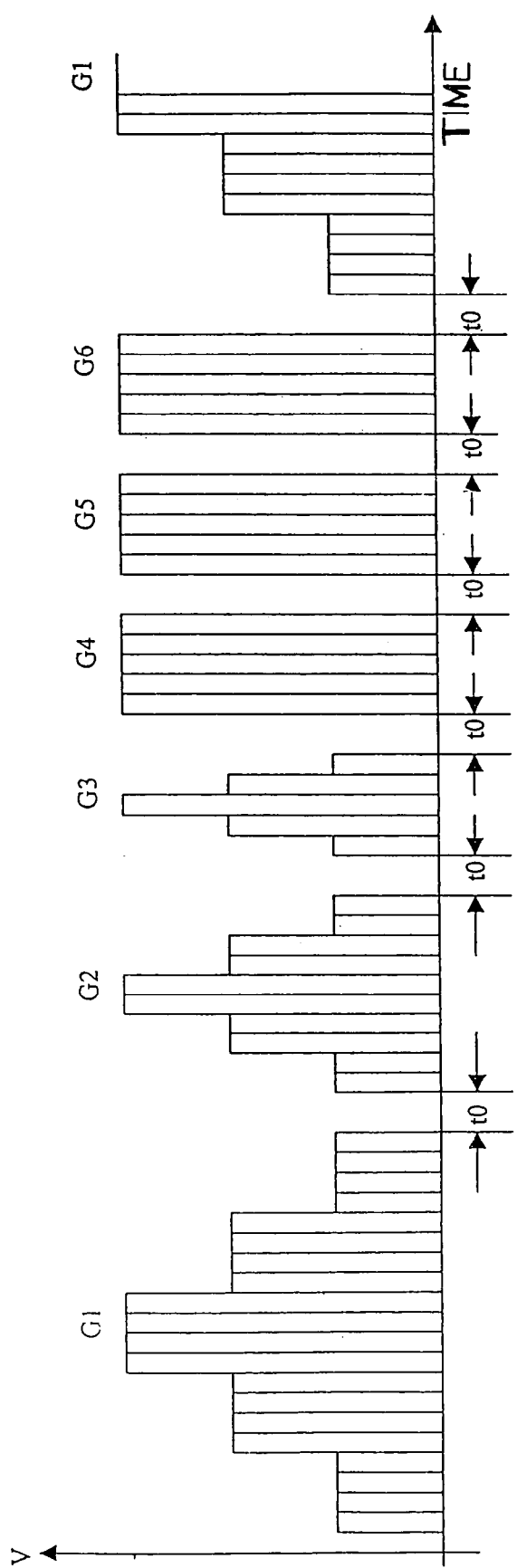
FIG. 5 illustrates another composite pulse formed by using the device for enhancing cell metabolism according to the above preferred embodiment of the present invention.

FIG. 5 illustrates another type of composite pulse output by the electrical pulse generating device 10 to the cosmetic function head 40 according to the preferred embodiment of the present invention. When producing the composite pulse as shown in FIG. 5, it is required that integrated circuit 15 controls the electrical pulse generating device 10 and the waveform adjuster 30 so as to first produce composite pulse sequences G1–G3, and output to the sixth level converter 46 a high electrical level signal that lasts for time t0.

According to the desired frequency and amplitude of composite pulse, the integrated circuit 15 then chooses a suitable pulse generator from the first to fifth pulse generators 11–15 to produce a pulse signal. According to the preferred embodiment of the present invention, the suitable pulse generator is the first pulse generator 11. At the same time, time sequence control converter 33 directly communicates with the level converter having the required electrical level. According the preferred embodiment of the present invention, the level converter having the required electrical level is the third level converter 43. As a result, the fourth to sixth composite pulse G4–G6, as shown in FIG. 5.

Furthermore, the same fourth to sixth composite pulses G4–G6 can also be produced by adjusting all of the electrical levels of the first to the fifth level converter 41–45 to be the same, such as 4V, and controlling the first to fifth level converter 41–45 with the time sequence control converter 33 to sequentially conduct. By continuous control in this manner, the first to third composite pulse G1–G3 and the fourth to sixth composite pulse G4–G6, as shown in FIG. 5, can be produced periodically.

Figure 6:
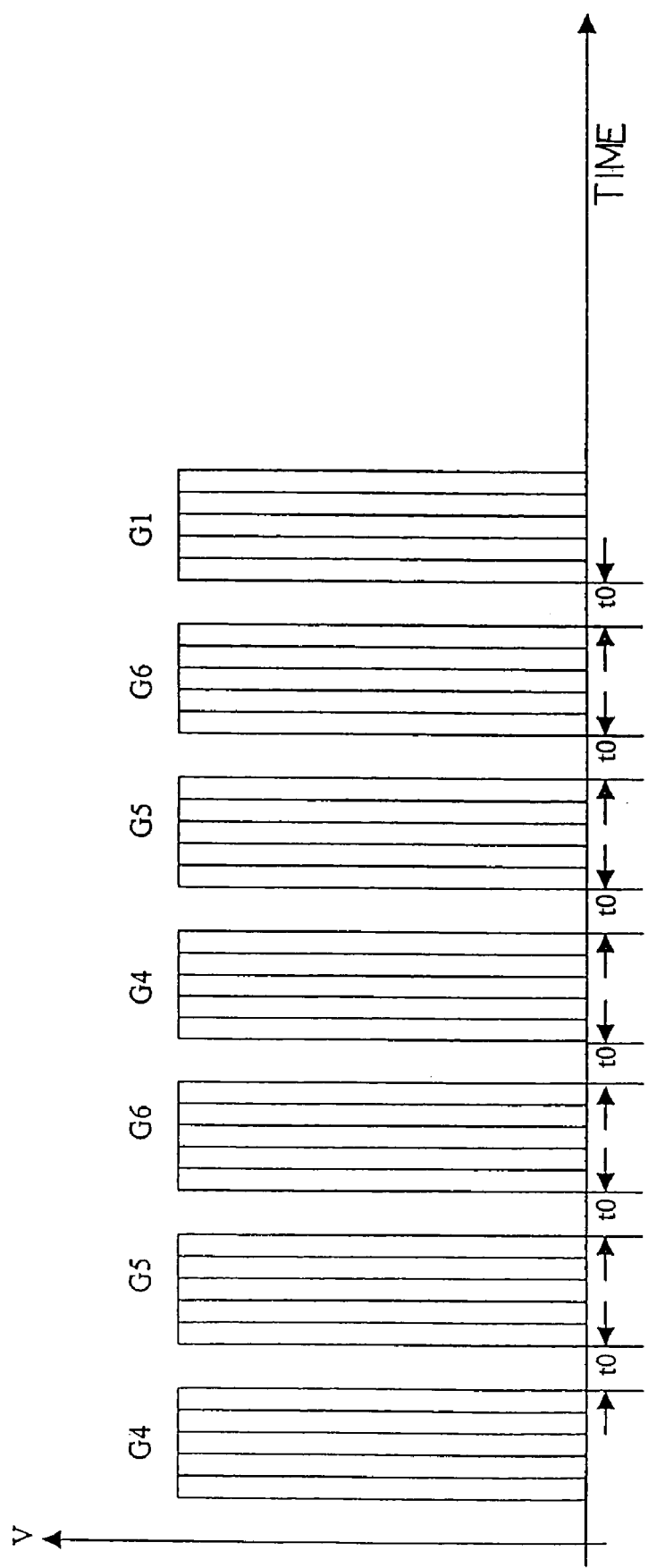
FIG. 6 illustrates yet another composite pulse formed by using the device for enhancing cell metabolism according to the above preferred embodiment of the present invention.

If the frequency of the pulse signal produced by the electrical pulse generating device 10 and the electrical level of the waveform adjuster 30 are kept constant, a pulse signal, as shown in FIG. 6, will be produced.

However, by adjusting the electrical level L1–L5 of the level converters 41–45, the shape and amplitude of the composite pulse outputted by the waveform synthesizer 47 can be altered.

In other words, by suitably adjusting the number of pulse generators of the electrical pulse generating device 10, the frequency of the pulse signal produced by the pulse generators, the number of level converters and their electrical levels of the waveform adjuster 30, and the frequency dividing number m and n of the first and second counter-controller 31 and 32 respectively, the present invention can produce composite pulse of any desired frequency, amplitude and shape.

The above preferred embodiment described the device for enhancing cell metabolism is exemplary only and not intended to be limiting. According to the above mentioned preferred embodiment, many parameters of the device can be altered to suit different needs. As an example, the number of pulse generators of the electrical pulse generating device 10 can be altered according to the frequency of the electrical pulse required by the device. The number can be less than or more than 3. The frequency of the pulse produced by each pulse generators can also be altered as desired.

When the number of pulse generators of electrical pulse generating device 10 is three, the frequency of the pulse signal produced by each pulse generators can be 1 MHz, 2 MHz and 4 MHz respectively, or 2 MHz, 4 MHz and 8 MHz respectively, and so on. The electrical levels of each of the level converter can be adjusted as desired, such as adjusting between 4 V–8 V. Also, the time lag, t0, between each composite pulse sequence can also be adjusted.

Figure 7:
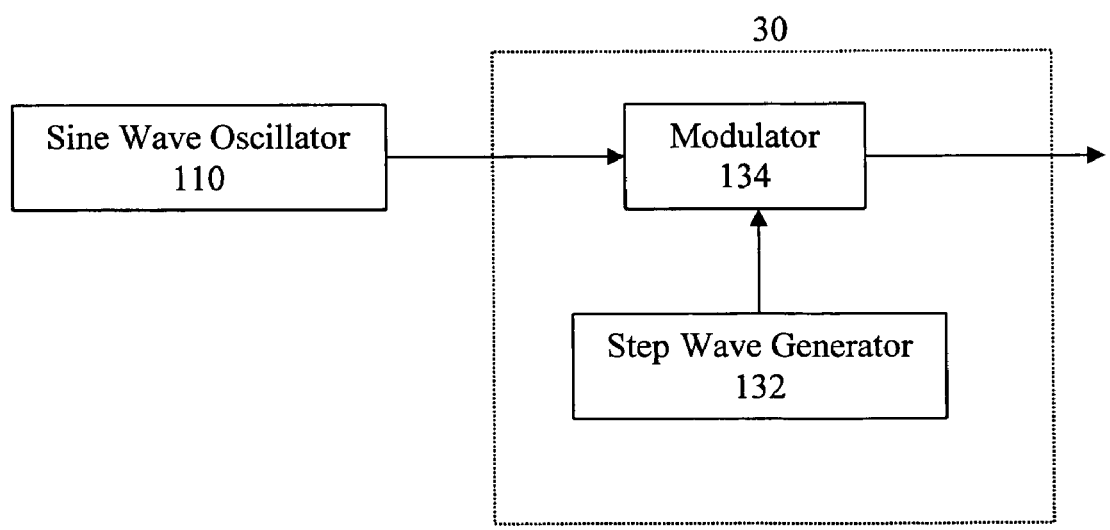
FIG. 7 is a circuit diagram of the device for enhancing cell metabolism according to a first alternative embodiment of the present invention.

FIG. 7 is a circuit diagram of the composite pulse generating device, according to a first alternative embodiment of the present invention. As shown in FIG. 7, the electrical pulse generating device 10 of the composite pulse generating device comprises a sine wave oscillator 110 and the waveform adjuster 30 comprises a step wave generator 132 and a modulator 134.

A wave carrier signal of the circuit is a high frequency sine wave signal produced by the sine wave oscillator 110. A modulating signal is a step wave produced by the step wave generator 132. The signal inputted to the cosmetic head 40 of the device is a high frequency signal wherein the amplitude of the high frequency signal is step wave modulated, and the frequency of the high frequency signal is the same as the frequency of the wave carrier signal provided by the sine wave oscillator 110.

The sine wave oscillator 110 and the step wave generator 132 can be comprised of integrated circuits or discrete components. The sine wave signal produced by the sine wave oscillator 110 can be of mono frequency. It can also be of different frequencies at different time.

According to this first alternative embodiment, the frequencies of sine wave signal produced by the sine wave oscillator 110 is preferably from one of or the combination of 666 KHz, 1 MHz, 2 MHz, 4 MHz and 8 MHz. The amplitude of the sine wave signal is preferably between 4–8V. The frequency of the first and fifth steps of the step wave signal produced by the step wave generator 132 is preferably 2–4V. The frequency of the second and fourth steps of the step wave signal produced by the step wave generator 132 is preferably 3–5V. The frequency of the third step of the step wave signal produced by the step wave generator 132 is preferably 4–8V.

The width of the step wave signal produced by the step wave generator 132 is a whole number multiple of the period (a reciprocal of the frequency) of the sine wave signal produced by the sine wave oscillator 110.

According to this embodiment, when compared with the preferred embodiment as shown in FIG. 2, the step width of the step wave signal produced by the step wave generator 132 is the fifteenth multiple of the period of the sine wave signal produced by the sine wave oscillator 110. Of course, the step width of the step wave signal can be adjusted as desired.

Figure 8:
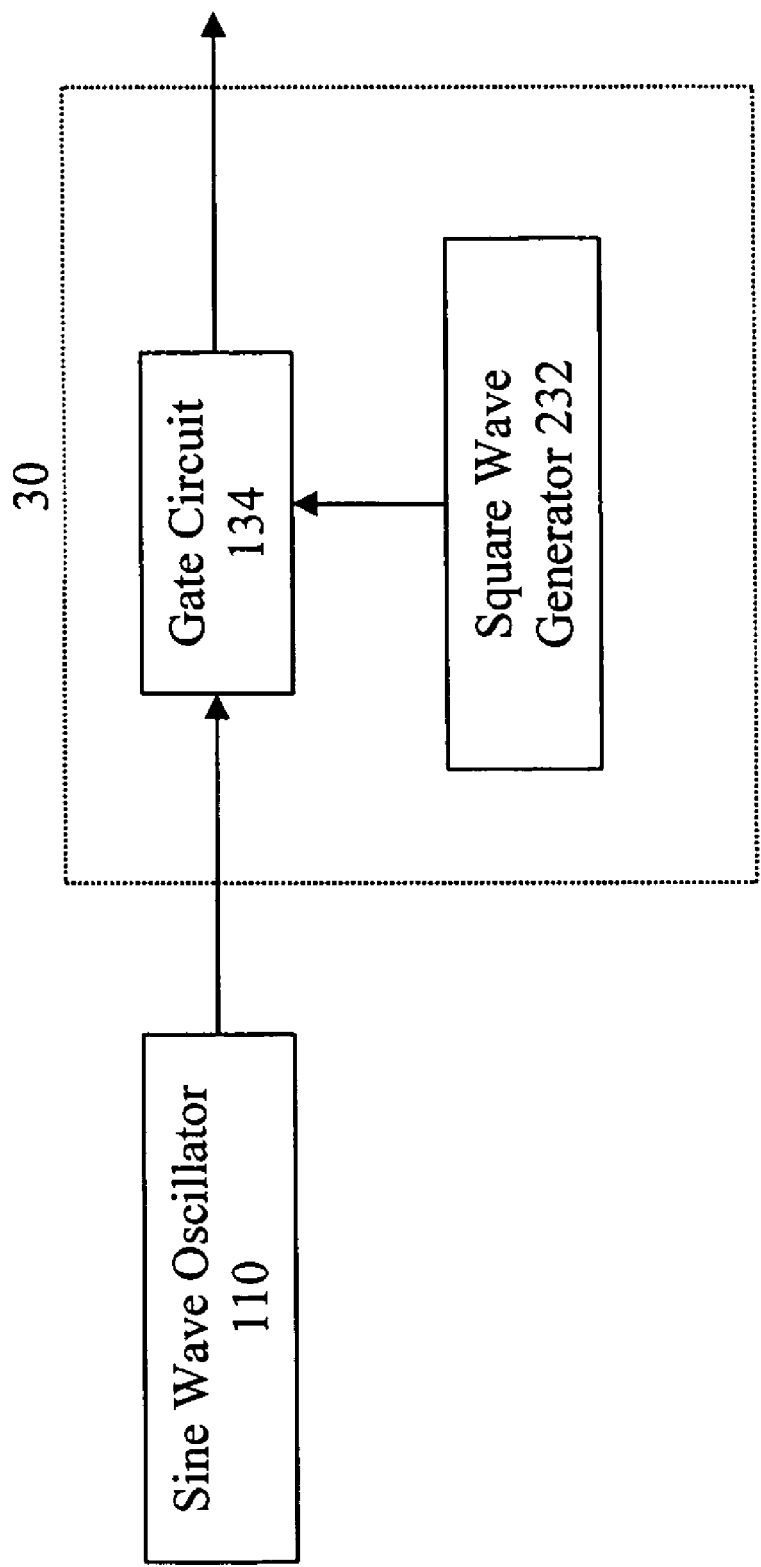
FIG. 8 is a circuit diagram of the device for enhancing cell metabolism according to a second alternative embodiment of the present invention.

FIG. 8 is a circuit diagram of the composite pulse generating device, according to a second alternative embodiment of the present invention. As shown in FIG. 8, the circuit of the composite pulse generating device according to this third embodiment is basically the same as the circuit of the composite pulse generating device according to the first alternative embodiment. The only differences are that the step wave generator 132 is replaced by a square wave generator 232 and the modulator 134 is replaced by a gate circuit 234, wherein the square wave generator 232 outputs a square signal which acts as a triggering signal for the gate circuit 234, wherein the frequency of the square signal is preferably 4–8V, and the period is preferably a whole number multiple of 12.5 µs, wherein the maximum period is 300 µs, the error of the maximum period is within ±10%. The width of the square pulse can eliminate the period of the square signal by 7 µs±3 µs.

The gate circuit 234 is a NAND gate which comprises of integrated circuits or discrete components. When the triggering signal from the square wave generator 232 is of high electrical level, the gate circuit 234 opens, which allows the passage of the high frequency signal of the sine wave oscillator 110. The direction of the high frequency signal is then reversed and outputted as positive signal.

When the triggering signal from the square wave generator 232 is of low electrical level, the gate circuit 234 closes, which interrupts the passage of the high frequency signal of the sine wave oscillator 110. As a result, the gate circuit 234 outputs a discontinuous high frequency signal, wherein the frequency of the high frequency signal is the same as the frequency of the sine wave signal produced by the sine wave oscillator 110. The discontinuity of the high frequency signal is controlled by the triggering signal produced by the square wave generator 232.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A cell enhancing device for enhancing human cell metabolism, comprising:

a treatment body having a treating head for contacting a skin of a user;

a pulse generating unit electrically connected to a power source for generating an electric pulse, wherein said electrical pulse generating unit comprises at least two electrical pulse generators, each generates a pulse signal having a unique frequency, wherein said pulse signals combine to form said electrical pulse; and a waveform adjuster electrically connected to said pulse generating unit for selectively tuning said electric pulse to form a composite pulse having an amplitude matching with an electrical pulse of a user, wherein said composite pulse is output at said treating head of said treatment body for communicating with a cell under said skin of said user so as to enhance a metabolism of said cell of said user, wherein said waveform adjuster comprises at least two level converters each having a unique electrical level, and a time sequence control converter, provided for choosing at least one of said level converters and controlling a conduction order of said chosen converters, wherein said waveform adjuster comprises a first, a second, a third, a fourth, a fifth and a sixth level converters, wherein a first and a fifth electrical levels of said first and said fifth level converters are equal, a second and a fourth electrical levels of said second and fourth level converters are equal, said first and third electrical levels of said first and third electrical levels are of an incremental relationship, and a sixth electrical level of said sixth level converter is 0V.

2. A cell enhancing device for enhancing human cell metabolism, comprising:

a treatment body having a treating head for contacting a skin of a user;

a pulse generating unit electrically connected to a power source for generating an electric pulse, wherein said electrical pulse generating unit comprises at least two electrical pulse generators, each generates a pulse signal having a unique frequency, wherein said pulse signals combine to form said electrical pulse; and a waveform adjuster electrically connected to said pulse generating unit for selectively tuning said electric pulse to form a composite pulse having an amplitude matching with an electrical pulse of a user, wherein said composite pulse is output at said treating head of said treatment body for communicating with a cell under said skin of said user so as to enhance a metabolism of said cell of said user, wherein said waveform adjuster comprises at least two level converters each having a unique electrical level, and a time sequence control converter, provided for choosing at least one of said level converters and controlling a conduction order of said chosen converters, wherein said electrical pulse generating unit further comprises an integrated circuit, wherein said electrical pulse generators are mounted on said integrated circuit, wherein said integrated circuit controls the pulse generation of said electrical pulse generators, wherein said waveform adjuster further comprises a second counter-controller producing a converter instruction signal to control the switching operation of said time sequence control converter, and a first counter-controller producing an integrated circuit instruction signal to control the switching between said pulse generators, wherein said waveform adjuster comprises a first, a second, a third, a fourth, a fifth and a sixth level converters, wherein a first and a fifth electrical levels of said first and said fifth level converters are equal, a second and a fourth electrical levels of said second and fourth level converters are equal, said first and third electrical levels of said first and third electrical levels are of an incremental relationship, and a sixth electrical level of said sixth level converter is 0V.

3. The cell enhancing device, as recited in claim 2, wherein said first and fifth electrical level of said first and fifth level converters are equal to said second and fourth electrical level of said second and fourth level converters, and are 3V, and said third electrical level of said third level converter is 4V.

* * * * *